United States Patent [19]

Pavia et al.

[11] Patent Number: 5,637,564
[45] Date of Patent: Jun. 10, 1997

[54] AMPHIPHILIC COMPOUNDS DERIVED FROM AMINO ACIDS OR PEPTIDES, THEIR METHODS OF SYNTHESIS AND THEIR APPLICATION AS DRUG DELIVERY SYSTEMS

[75] Inventors: Andre A. Pavia, Villeneuve-lez-Avignon; Bernard Pucci, Molleges; Jean G. Riess, Falicon; Leila Zarif, Laurent du Var; Camille Guedj, Pont-Saint-Esprit, all of France

[73] Assignee: Alliance Pharmaceutical Corp., San Diego, Calif.

[21] Appl. No.: 470,140

[22] Filed: Jun. 6, 1995

Related U.S. Application Data

[63] Continuation of Ser. No. 100,688, Aug. 2, 1993, Pat. No. 5,446,023.

[30] Foreign Application Priority Data

Aug. 6, 1992 [FR] France ......................... 92 09776

[51] Int. Cl.$^6$ ............................. A61K 38/00; A61K 38/02
[52] U.S. Cl. .................................. 514/8; 514/13; 514/14; 514/15; 514/16; 514/17; 514/18; 514/19
[58] Field of Search ................................ 514/13–19, 8

[56] References Cited

U.S. PATENT DOCUMENTS

| 2,785,152 | 3/1957 | Jonas. | |
|---|---|---|---|
| 2,830,983 | 4/1958 | Lemieux. | |
| 5,446,023 | 8/1995 | Pavia et al. | 514/13 |

FOREIGN PATENT DOCUMENTS

| 0255443 | 7/1987 | European Pat. Off.. |
| 9000396 | 1/1990 | WIPO. |
| 9015807 | 12/1990 | WIPO. |
| 9116347 | 10/1991 | WIPO. |

OTHER PUBLICATIONS

Ferrari, B., et al. Artificial carbohydrate antigens: the synthesis of glycopeptidic haptens with $T_N$ specificity. Bio. Org. Chem. 11(1):85–95 (1982).

Kiwada, et al. Application of synthetic liposomes based on acyl amino acids or acyl peptides as drug carriers. Chem. Pharm. Bull., 35:2935–1942 (1987).

Larrabee, C.E., et al. Radiation–induced polymerization of sodium 10–undecenoate in aqueous micelle solutions. J. Polymer Sci. Polyn. Lett. Ed. 17:749–751 (1979).

LeBlanc, M. et al. Use of lymphoblastoid Namalva cell cultures in a toxicity test. Application to the monitoring of detoxification procedures for fluorocarbons to be used as intravascular oxygen–carriers. Pharm. Res. 246 (1985).

Liposome Technology. Targeted Drug Delivery and Biological Interaction. vol. III. (G. Gregoriadis ed., CRC Press, Inc., (1984).

Ogawa, T., et al. Enhancement of serum antibody production in mice by oral administration of lipophilic derivatives of muramylpeptides and bacterial lipopolysaccharides with bovine serum albumin. Chem. Abstracts 105:305q (1986).

Okahata, Y., et al., Functional capsule membranes. Part 29. Concanavalin A–induced permeability control of capsule membranes corked with synthetic glycolipid bilayers or grafted with synthetic glycopolymers. J. Chem. Soc. Perkin Trans. II p. 1317 (1987).

Ozer, et al., A novel drug delivery system: non–ionic surfactant vesicles. European Journal of Pharmaceutical and Biopharmaceutics. 37:75–79 (1991).

Okahata, Y., et al., Functional capsule membranes. Part 28.[1] A capsule membrane grafted with viologen–containing polymers as a reactor of electron–transfer catalysis in heterophases. J. Chem. Soc. Perkin Trans. II p. 1003 (1987).

*Primary Examiner*—Jerry D. Johnson
*Attorney, Agent, or Firm*—Knobbe, Martens, Olson & Bear

[57] ABSTRACT

Amphiphilic derivatives of amino acids or peptides are provided, comprising a polyhydroxylated hydrophilic part derived from a sugar, from a polyol, from an aminopolyol or from an oligosaccharide, and at least one hydrophobic part derived from a hydrocarbon, fluorocarbon, or a mixed fluorocarbon/hydrocarbon, saturated or unsaturated, having from 5 to 20 carbon atoms, the hydrophobic part(s) being linked to the hydrophilic part by a junction bearing an amino acid or a peptide.

19 Claims, No Drawings

AMPHIPHILIC COMPOUNDS DERIVED FROM AMINO ACIDS OR PEPTIDES, THEIR METHODS OF SYNTHESIS AND THEIR APPLICATION AS DRUG DELIVERY SYSTEMS

This application is a continuation of application Ser. No. 08/100,688, filed Aug. 2, 1993, now U.S. Pat. No. 5,446,023.

This application claims priority to French application No. 92-09776 which was filed Aug. 6, 1992.

The present invention relates to the field of biologically compatible surfactants, comprising amphiphilic structures derived from biologic molecules. It relates particularly to amphiphilic derivatives of amino acids or of peptides, useful in drug preparations or in cosmetic formulations.

BACKGROUND OF THE INVENTION

Amphiphilic amino acid and peptide derivatives have surfactant properties that make them utilizable, alone or with other substances, as emulsifiers or co-emulsifiers, as dispersants or solubilizers, as modifiers of natural or synthetic membranes or in forming drug vehicles or targeting devices. Some of them are capable of forming vesicles (a structure equivalent to that of the liposomes obtained from phospholipids).

A drug vehicle provides advantages in therapy, among them prolonged intravascular persistence and a controlled release of the drug, resulting in greater efficacy and reduced doses, which is of great importance when the drug is toxic or provokes side effects. The pharmacokinetics and biodistribution of the encapsulated drug are determined by the drug vehicle, and thus on the structure of the molecules that compose this vesicle. Thus, in order to enhance the specificity of the vesicles for targeting cells, derivatives of carbohydrates are incorporated in vesicles containing an imaging agent or a therapeutic agent (see Liposome Technology, Targeted Drug Delivery and Biological Interaction, Vol. III, G. Gregoriadis ed., CRC Press, Inc., 1984).

The present invention deals with new amphiphiles that can be used as drug vehicles and for the specific targeting of a drug by virtue of a terminal sugar group which is recognized by specific receptor on the cell membrane. The new amphiphiles comprise a carbohydrate part and a peptidic spacer between the hydrophilic saccharidic head and the hydrocarbon and/or fluorocarbon hydrophobic tail. Hydrocarbon molecules with a sugar head have been described by Okahaya et al (J. Chem. Soc. Perkins Trans. 2 (1987) p. 1317), but they do not bear a peptidic spacer. Amphiphilic compounds derived from sugars and bearing a fluorocarbon chain, but with no peptidic spacer, have been described in EP-A-0255443. In the amphiphilic compounds of the invention, the peptidic spacer allows the modulation of the hydrophilic/lipophilic balance of the molecule and thus contributes to determining the structure of the dispersion obtained.

The amphiphilic compounds of the invention can also be used as emulsifiers or co-emulsifiers, as for example in oxygen-transport systems based on fluorocarbons. Such systems presently exist, but they present certain disadvantages, specifically, the surfactants used are not particularly adapted to the emulsification of fluorocarbons, and do not allow modification of the characteristics of the emulsions in order to adapt them to specific therapeutic applications.

The present invention has as its specific object amphiphile derivatives of amino acids of peptides, suitable in particular for the fixation, dispersion, encapsulation and targeting of pharmaceutical products and the emulsification of fluorocarbons.

SUMMARY OF THE INVENTION

The invention provides amphiphilic compounds derived from an amino acid or a peptide and having the formulas I or II, and comprising a polyhydroxylated hydrophilic moiety, an amino acid or peptide moiety and a bivalent radical derived from a monosaccharide in open form and having one of the formulas III–V. At least one of the $R^2$ and $R^3$ substituents in formula I and II is a hydrocarbon, fluorinated hydrocarbon, or fluorocarbon radical as described below. $R^4$, $Y^1$, and $Y^2$ of formula II are selected from the radical species set forth in (f) and (g) below.

In a preferred embodiment, X is a $C_1$ to $C_{24}$ sugar, a polyol selected from a hydrogenated sugar, a cyclic hexitol, or a sugar or polyol in which one or more H atoms of the polyol or sugar OH groups have been substituted as described below. In particularly preferred embodiments, X is a galactose, glucose, or mannose group. In a particularly preferred embodiment, $R^1$ is a glucose radical of the formula III–V.

In other embodiments, the amphiphile contains a radical of a standard amino acid or an analogue thereof comprising a linear or branched alkyl group, or other substituted alkyl groups, as disclosed herein, or peptides made up of standard or substituted amino acids. In yet other embodiments, the amphiphiles comprise $R^2$ and $R^3$ that are terminal radical groups comprising multiple —$(CH)_2$— groups or unsaturated sites. The amphiphiles of the invention also comprise glucamine structures, for example

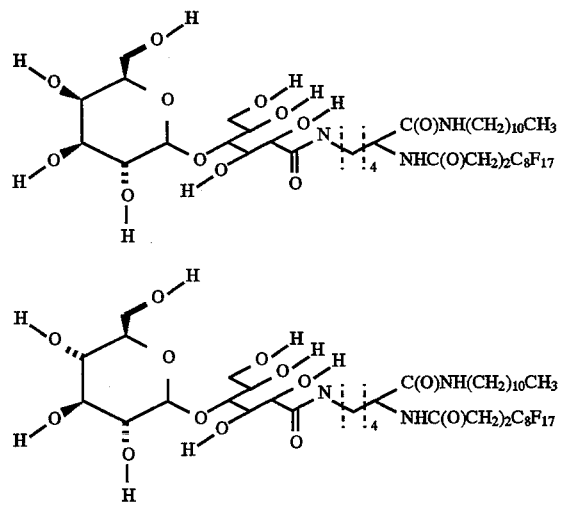

The invention also provides methods for preparing the amphiphilic compounds of the invention.

According to another aspect of the invention there are provided compositions for biomedical use containing the amphiphilic compounds of the invention. These amphiphiles can be in the form of lipid vesicles, and can be alone or in combination with other natural or synthetic amphiphilic compounds. These compositions have the advantage of being stable through heat sterilization. They can also contain various drugs, for example, antitumor agents, as well as agents to control pH, osmotic pressure, and oxidation. These compositions, according to a specific embodiment, can be used in methods to modify natural or synthetic membranes.

Also within the scope of the invention are emulsions comprising an aqueous phase, an oily phase, and one or more amphiphiles of the invention which acts as a surfactant. The oily phase of the emulsion can be a fluorocarbon. The fluorocarbon is preferably perfluoctylbromide or perfluorooctylethane. The emulsion can contain another surfactant, for example, lecithin. In particularly preferred embodiments, the concentration of amphiphile in the emulsion is from 0.01% to 30% w/v, and the concentration of fluorocarbon is from 10% to 125% w/v.

DETAILED DESCRIPTION OF THE INVENTION

The amphiphilic compounds of the invention comprise a polyhydroxylated hydrophilic part, which is an open ring sugar, a polyol, an aminopolyol or an oligosaccharide, and at least one hydrophobic part, which is a hydrocarbon, a fluorocarbon or a partially fluorocarbonated hydrocarbon, saturated or unsaturated, having from 5 to 20 carbon atoms. The hydrophobic part(s) are joined to the polyhydroxylated hydrophilic part by a linking group comprising an amino acid or a peptide.

In these compounds, the presence of a hydrophilic part derived from an open ring sugar makes it possible for the amphiphilic derivative to be used as a drug vehicle and achieve targeting of the cells. Certain glycosidic structures have indeed the advantage of being recognized by membrane receptors such as lectins.

The presence of an amino acid- or peptide-type spacer, separating the hydrophilic part from the hydrophobic extremity also allows modification of the hydrophilic-lipophilic balance of the compound, and thus of its solubility.

According to the invention, the amino acid or peptide derivative can correspond to one of the following formulae:

$$X-R^1-AA-Y^1-\underset{\underset{R^3}{|}}{\overset{\overset{R^2}{|}}{CH}} \quad (I)$$

or $$X-R^1-R^4-\underset{\underset{Y^3R^3}{|}}{\overset{\overset{Y^2R^2}{|}}{CH}} \quad (II)$$

wherein a. X is a polyhydroxylated hydrophilic moiety selected from the group consisting of a sugar, a polyol, an aminopolyol or an oligosaccharide;

b. $R^1$ represents a bivalent radical derived from a monosaccharide in an open form and having the formula:

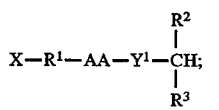

$-CH_2(CHOH)_4-C(O)-$; (IV)

or

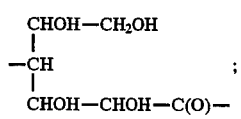
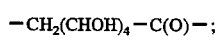

c. AA is an amino acid or peptide moiety;

d. $Y^1$ is —NH—, —S—, —CO—, —C(O)—$(CH_2)_L$—, wherein L is 1 or 2, or —O—;

e. $R^2$ and $R^3$, which can be identical or different, are H; a linear or branched, saturated or unsaturated $C_{5-20}$ hydrocarbon; or a linear or branched, saturated or unsaturated $C_{5-20}$ fluorinated hydrocarbon or fluorocarbon radical wherein 50 to 100% of the hydrogen atoms have been replaced by fluorine atoms, said hydrocarbon, fluorinated hydrocarbon or fluorocarbon radical optionally having one or more O and S atoms within the C chain, and optionally having the hydrogen atoms of said radical replaced by one or more chlorine or bromine atoms; and an unsaturated terminal group having the formula:

—O—CH=$CH_2$;

—OC(O)$CR_5$=$CH_2$;

—C(O)—$CR_5$=$CH_2$; or;

—NHC(O)$CR_5$=$CH_2$ in which $R^5$ is H or $CH_3$, provided that $R^2$ and $R^3$ do not both represent H;

f. $R^4$ represents

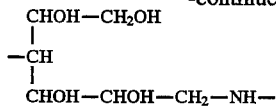

—O—CH$_2$—;

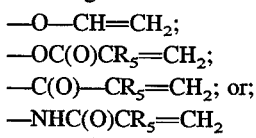

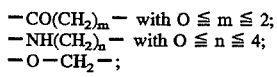

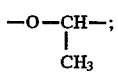

—NH—$CH_2$—CH(OH)—$(CH_2)_2$—;

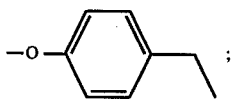

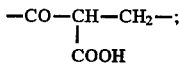

—AA—CO—$(CH_2)_m$ with $0 \leq m \leq 2$;

—AA—NH—$(CH_2)_n$— with $0 \leq n \leq 4$;

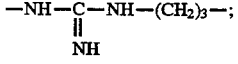

—AA—NH—$CH_2$—CH(OH)—$(CH_2)_2$—;

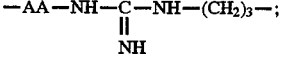

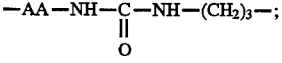

-continued

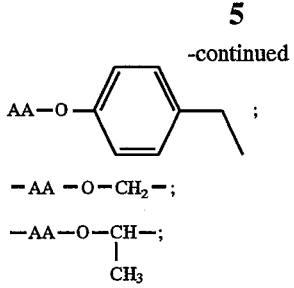

$-AA-O-CH_2-$;

$-AA-O-CH-$
              |
              $CH_3$ wherein AA is an amino acid or peptide;

g. $Y^2$ and $Y^3$, which are different, are $-(CH_2)_mC(O)-NH-$ with $0 \leq m \leq 2$;
$-(CH_2)_mC(S)-NH-$ with $0 \leq m \leq 2$;
$-(CH_2)_pO-$ with $0 \leq p \leq 2$;
$-(CH_2)_pOC(O)-$ with $0 \leq p \leq 2$;
$-(CH_2)S-$;
$-C(O)O-$;
$-C(O)S-$;
$-(CH_2)_nNHC(O)-$ with $0 \leq n \leq 4$;
$-(CH_2)_2-CH(OH)-CH_2-NH-C(O)-$;

$-(CH_2)_3-NH-\underset{\underset{NH}{\|}}{C}-NH-C(O)-$;

$-(CH_2)_3-NH-C(O)-NH-C(O)-$;

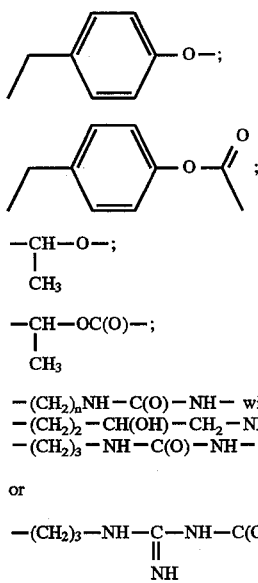

$-CH-O-$
  |
  $CH_3$ $-CH-OC(O)-$
  |
  $CH_3$ $-(CH_2)_nNH-C(O)-NH-$ with $0 \leq n \leq 4$;
$-(CH_2)_2-CH(OH)-CH_2-NH-C(O)-NH-$;
$-(CH_2)_3-NH-C(O)-NH-C(O)-NH-$;

or $-(CH_2)_3-NH-\underset{\underset{NH}{\|}}{C}-NH-C(O)-NH-$ provided that at least one of the $Y^2$ and $Y^3$ represent $-NH-C(O)-$ or $-C(O)-NH-$.

As will be seen hereafter, in the derivatives of formula (I) the amino acid or peptide spacer terminates at the level of the hydrophobic part with an amino acid comprising only the two acid and amine functional groups.

In the derivatives of formula (II) the amino acid- or peptide-spacer is terminated at the level of the hydrophobic part by an amino acid having a functionalized side chain.

The derivatives of formula (I) and of formula (II) can comprise either a single hydrophobic end (when $R^2$ or $R^3$ represents H) or two hydrophobic ends (when $R^2$ and $R^3$ are both hydrocarbon or fluorocarbon radicals). Thus, the degree of their hydrophobic or fluorophilic nature can be regulated.

In the amphiphilic compounds of the invention, the polyhydroxylated hydrophilic portion of the molecule corresponding to X can be derived from a saturated or unsaturated sugar, from $C_1$ to $C_{24}$, that is a member of the series of tetroses, pentoses, hexoses, aminopentoses, aminohexoses, desoxypentoses, desoxyhexoses, disaccharides and oligosaccharides;

a polyol constituting the hydrogenated form of a sugar of the series of tetroses, pentoses, hexoses, aminopentoses, aminohexoses, desoxypentoses, desoxyhexoses, disaccharides and oligosaccharides;

a cyclic hexitol; or sugars and polyols described above in which one or several hydrogen atoms of the OH polyol or sugar groups have been replaced by an acetyl, benzyl, allyl, benzoyl, trityl, isopropylidene, benzylidene or cyclohexylidene group, by a group of formula $(CH_2CH_2O)_tR^6$ with t being an integer from 1 to 100 and $R^6$ a hydrogen atom, a linear or branched, saturated or unsaturated $C_1$ to $C_{24}$ hydrocarbon radical.

Preferred sugars derived from the tetrose series are, for example, erythrose or threose; those of the pentose series are arabinose, lyxose, ribose, xylose or fructose; those of the hexose series are allose, altrose, galactose, glucose, gulose, idose, mannose, or talose; those of the aminopentose or aminohexose series are, for example, galactosamine, glucosamine or mannosamine; those of the deoxypentose or the deoxyhexose series are fucose or rhamnose. Preferred sugars of the disaccharide or oligosaccharide series are cellobiose, lactose, maltose, melibiose, palatinose, saccharose, trehalose, turanose, maltotriose and maltotetraose; the preferred hydrogenated forms of the sugars mentioned above are erythritol, threitol, arabinitol, ribitol, xylitol, altritol, galactitol, glucitol, gulitol, iditol, mannitol, galactamine and glucamine. Preferred polyols of the cyclic hexitol series are for example myo-inositol. These radicals derived from sugars can be in either the D or the L form.

The choice of the monosaccharide, polyol, aminopolyol or oligosaccharide for X depends in particular on the applications of the compound. When the derivative is to be used for the encapsulation of pharmaceutical products, X preferably represents galactose, glucose or mannose, which are recognized by the lectin receptor.

This hydrophilic part X is joined to the spacer, consisting of an amino acid or a peptide, by a radical derived from a monosaccharide in an open form, of aldonic or glycamine type, comprising a CO or a NH group at the end linked to the AA or $R^4$ part. This group permits the formation of bonds of amide $-CO-NH-$ or $-NH-CO-$ type with the amino acid or peptide part of the derivative.

As an example, $R^1$ can be derived from glucose and correspond to one of the following formulas:

$$\begin{array}{l} CHOH-CH_2OH \\ | \\ -CH \\ | \\ CHOH-CHOH-C(O)- \end{array} \quad \text{(III)}$$

$$-CH_2(CHOH)_4-C(O)- \quad \text{(IV)}$$

or $$\begin{array}{l} CHOH-CH_2OH \\ | \\ -CH \\ | \\ CHOH-CHOH-CH_2-NH- \end{array} \quad \text{(V)}$$

In the amphiphilic compounds of the invention, AA represents a radical of an amino acid or a peptide, or a radical of formula:

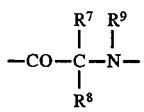

in which $R^7$ and $R^8$ represent a hydrogen atom or the side chain of an amino acid, optionally having other functional groups, and $R^9$ represents a hydrogen atom or forms with $R^7$ a cyclic hydrocarbon radical.

The term "amino acid" used here concerns the alpha amino acids commonly found in proteins, which are generally known as standard amino acids, and their analogues. It also includes modified standard amino acids having side chains comprising groups that are linear and branched alkyl groups, hydroxyalkyl, carboxyalkyl, aralkyl, aminoalkyl, carboxamide alkyl, mercaptoalkyl, phenylalkyl, hydroxyphenylalkyl, guanidinoalkyl, imidazoylalkyl, indolylalkyl, and pyrrolidinyl.

Among the amino acids that can be used are alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenylalanine, homoarginine, thiazolidine and dehydroproline.

When AA represents a radical derived from a peptide, the latter is formed from the amino acids described above and generally comprises from 2 to 10 amino acids, preferably from 2 to 3 amino acids.

In the amphiphilic compounds of the invention corresponding to formulae (I) and (II) at least one of $R^2$ and $R^3$ represents a linear or branched, saturated or unsaturated hydrocarbon or fluorocarbon radical, which constitutes the hydrophobic part of the molecule.

These radicals optionally have one or more heteroatoms, for example, oxygen or sulfur in their carbon chain, and can be substituted with chlorine or bromine atoms as well as fluorine atoms.

Fluorocarbon radicals of the following formulas are preferred:

a) $C(CF_2)_i$ in which i is an integer from 3 to 18, b) $(CF_3)_2CF—(CF_2)_j—$ in which j is an integer from 0 to 8, c) $R_{F1}(CF_2CF(CF_3))_k—$ in which $R_{F1}$ represents $CF_3—$, $C_2F_5—$ or $(CF_3)_2CF—$ and k is an integer from 1 to 4, d) $(R_{F2})(R_{F3})CFO(CF_2—CF_2)_L—$ in which $R_{F2}$ and $R_{F3}$ independently represent $CF_3—$, $C_2F_5$, n—$C_3F_7—$ or $CF_3CF_2CF(CF_3)—$, or $R_{F2}$ and $R_{F3}$ together form —$(CF_2)_4—$ or —$(CF_2)_5—$, and L is an integer from 1 to 6, e) $CF_3CF_2O(CF_2CF_2O)_uCF_2—$ in which u is an integer from 0 to 5, f) $CF_3(CF_2)_2O(CF(CF_3)CF_2O)_v—CF(CF_3)—$ in which v is an integer from 0 to 6, and g) the radicals of paragraphs a) to f) bearing at their extremity linked to the amino acid or peptide, a hydrocarbon arm of type —$(CH_2)_x—$ or —$(CH_2)_{x1}—S—(CH_2)_{x2}—$ with x, $x_1$ and $x_2$ being integers from 1 to 10.

Preferred radicals of this type are of the formulas:

—$CH_2—(CF_2)_i—F$

—$(CH_2)_2(CF_2)_i—F$

—$(CH_2)_2—S—(CH_2)_2—(CF_2)_i F$ with $3 \le i \le 18$.

When $R^2$ and/or $R^3$ represent a hydrocarbon radical, they are radicals of hydrocarbons which can be saturated, monounsaturated or polyunsaturated, the unsaturations being ethylenic or acetylenic, and the radicals either linear or branched.

These groups can also, like the fluorinated radicals described above, comprise an unsaturated terminal group corresponding to one of the following formulae:

—O—CH=$CH_2$,

—OC(O)$CR^5$=$CH_2$,

—C(O)—$CR^5$=$CH_2$, or

—NHC(O)$CR^5$=$CH_2$ wherein $R^5$ represents H or $CH_3$.

Preferred hydrocarbon radicals of this type are of the formulas:

—$(CH_2)_{i1}—CH$=$CH_2$ with $3 \le i_1 \le 18$

—$(CH_2)_{i2}—NH—C(O)—CH$=$CH_2$ with $2 \le i_2 \le 17$

—$(CH_2)_{i2}—C(O)—CH$=$CH_2$ with $2 \le i_2 \le 17$

—$(CH2)_{i3}H$ with $5 \le i_3 \le 20$.

The incorporation of unsaturated hydrocarbon radicals into the amphiphilic compounds of the inventions is advantageous because the amphiphiles comprising such radicals can be polymerized, for example, by irradiation with ionizing radiation. Thus, the properties of delayed release of substances in dispersions utilizing these polymerized derivatives can be further controlled.

Examples of compounds conforming to the invention are given in Table 1 and the synthetic schemes I and II.

The compounds of the invention can be prepared by classical procedures from modified amino acids or peptides and lactones or glucamines corresponding to $XR^1$.

Thus, compounds of formula (I), in which $Y^1$ represents NH, can be prepared by a procedure consisting, for example, of reacting an amino acid derivative of formula:

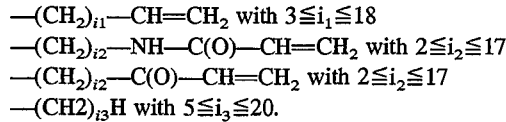 (VI)

in which $R^2$, $R^3$ and AA have the above signification, with a lactone derived from the oligosaccharide X-$R^1$, for example a lactone of formula (VII):

 (VII)

such as lactobiono-1,5-lactone or maltobiono-1,5-lactone.

For this reaction, the amino acid derivative of formula (VI) may be in the form of a salt, for example trifluoroacetate.

The amino acid derivative of formula (VI) can be prepared from the iodide $R^2I$ and the aldehyde $R^3CHO$ to form the azide of formula:

 (VIII)

which is then reduced and condensed with the amino acid or the peptide corresponding to AA whose $NH_2$ terminal group is protected by an appropriate protecting group such as butoxycarbonyl (BOC) or benzyloxycarbonyl (Z).

These reactions are illustrated in the synthetic scheme I (infra) in the case where AA represents Gly or GlyGly and in the case where XR' represents the lactobiono-1,5-lactone. When $XR^1$ represents maltobiono-1,5-lactone, the derivative of the invention corresponds to the formula:

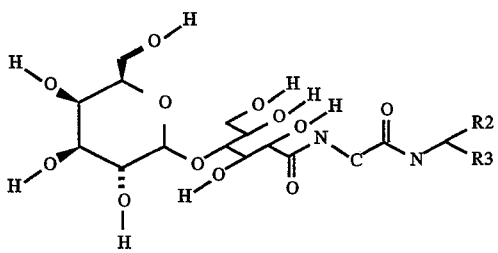

wherein $R^2$ represents
$(CH_2)_{11}CH_3$,
$(CH_2)_2C_6F_{13}$, or
$(CH_2)_2C_8F_{17}$
and $R^2$ represents $(CH_2)_8CH=CH_2$ or $(CH_2)_8CH_3$ The compounds of formula (I) in which X, $R^1$, AA, $R^2$ and $R^3$ have the above signification and $Y_1$ represents CO can be prepared by a procedure consisting in making an amino acid or peptide derivative of formula:

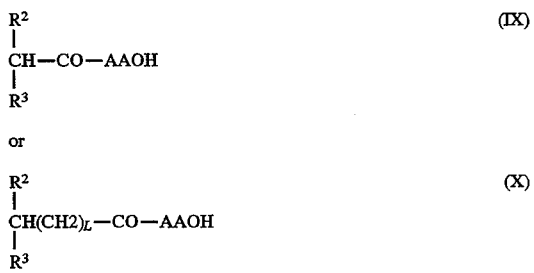

where $1 \leq L \leq 2$, react with a glucamine derived from oligosaccharide $R^1X$, for example a glucamine of formula (XI):

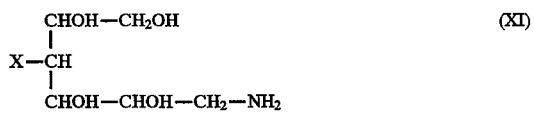

in the case where $R^1$ is a glucose radical.

The compounds of formula (IX) and (X) can be prepared from the corresponding acids of formula XII or XIII:

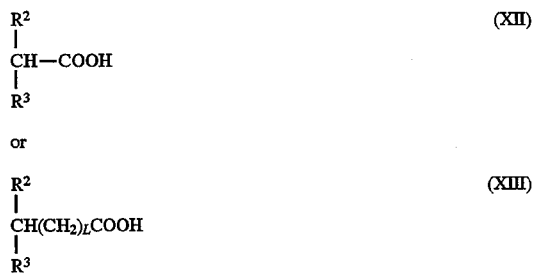

The acid of formula (XII) or (XIII) is then allowed to react with the amino acid or peptide corresponding to AA whose terminal COOH is protected by an appropriate group.

For the following reaction with glucamine, the COOH group is deprotected to react with the $NH_2$ group of the glucamine.

The compounds of formula (I) wherein $Y^1$ represents O or S can be prepared by a procedure analogous to that represented in synthetic scheme (I), but in which the condensation is effected directly at the level of the secondary alcohol or the secondary thiol obtained by nucleophilic substitution of this alcohol.

The compounds of formula (II), wherein X, $R^1$, $Y^2$, $Y^3$, $R^2$ and $R^3$ are as defined above, and $R^4$ is:

—CO(CH$_2$)$_m$ with $0 < m < 2$

—CO—CH—CH2—
      |
     COOH

—AA—CO—(CH$_2$)$_m$, and

—AA—CO—CH—CH$_2$—
            |
          COOH can be prepared by reacting an amino acid or a peptide derivative of formula (XIV):

in which $R^2$, $R^3$, $R^4$, $Y^2$ and $Y^3$ are as defined above, with a glucamine derived from the oligosaccharide X-$R^1$, for example the glucamine of formula XI:

when $R^1$ is derived from glucose.

The compounds of formula (XIV) can be prepared from the corresponding polyfunctional amino acids in which all the reactive functions, except that corresponding to $Y^2$, are protected, by making them react with a compound comprising the hydrocarbon or fluorocarbon radical $R^2$, for example an amine, an isocyanate or an isothiocyanate when $Y^2$ is derived from an acid, an acid when $Y^2$ is derived from an amine, an acid or an isocyanate when $Y^2$ is derived from an alcohol, and an acid when $Y^2$ is derived from a thiol.

Next, another reactive function of the amino acid or the peptide is deprotected to make it react with a compound bearing $R^3$, as above.

This process is illustrated, in the case where $R^4$ is derived from aspartic acid or glutamic acid, in the right-hand part of synthetic scheme II, attached.

Glucamines of formula (IX) can be synthesized from the corresponding saccharides by Lemieux's method, as described in the document U.S. Pat. No. 2,830,983.

The derivatives of formula (II) wherein $R^4$ represents:

—NH(CH$_2$)$_n$— with $0 \leq n \leq 4$;

—NH—CH$_2$—CHOH—(CH$_2$)$_2$—;

—NH—C—(CH$_2$)$_3$—;
      ||
     NH

—NH—C—NH—(CH$_2$)$_3$—;
      ||
     O

—AA—NH—(CH$_2$)$_n$— with $0 \leq n \leq 4$;

—AA—NH—CH$_2$—CHOH—(CH$_2$)$_2$—;

—AA—NH—C—(CH$_2$)$_3$—;
          ||
         NH or

-continued

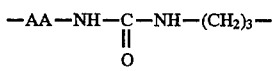

can be prepared by a procedure consisting of reacting an amino acid or peptide derivative of formula:

with a lactone derived from oligosaccharide X—$R^1$, for example the lactone of formula (V) when $R^1$ is a glucose radical. The compound of formula (XV) can be prepared from the corresponding polyfunctional amino acid by reaction with the appropriate compounds, making it possible to introduce the $R^2$ and $R^3$ groups on the two functions of the amino acid (other than an $NH_2$ function).

An example of synthesis corresponding to this procedure is illustrated in the left-hand part of synthetic scheme II, attached, in the case where the amino acid whose side chain is functionalized is lysine.

The derivatives of formula (II) of the invention in which $R^4$ represents

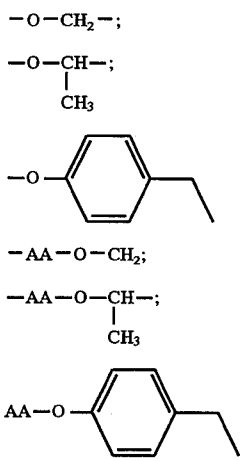

can be prepared by a procedure consisting in reacting groups $R^2$ and $R^3$ on the acid and amine functions $Y^2$ and $Y^3$ with the corresponding amino acid, then condensing the amino acid or peptide AA on the remaining alcohol function.

The compounds of the invention are advantageous for use in numerous applications because of their highly amphiphilic nature. In particular, they are powerful surfactants, soluble or dispersible in water, and can therefore be used for the preparation of emulsions or dispersions, including vesicles, containing pharmaceutical substances.

The present invention also concerns preparations for biomedical use comprising at least one amphiphilic compound according to the invention. These preparations can be in the form of solutions (including micellar ones), dispersions, gels and emulsions in water or any other appropriate solvent.

The compounds of the invention are also useful for preparing modifying lipidic membranes and vesicles which can be used as a drug vehicle, which can comprise oxygen carriers such as hemoglobin or modified hemoglobin or synthetic chelates. The vesicles can also be used in diverse fields for contrast agents and cosmetics.

Moreover, the invention also concerns preparations containing at least one amphiphilic amino acid or peptide derivative according to the invention, in the form of vesicles. These vesicles can incorporate drug in the inner aqueous phase or the lipid bilayers of the vesicles by methods which will be apparent to one skilled in the art.

Such preparations are useful as vehicle for drugs such as anti-inflammatory agents, analgesics, anti-allergics and anti-tumoral agents, and antibiotics, in particular anti-cancer agents such as cis-platinum, 5-fluorouracyl or its derivatives and adriamycin. In those systems, the drug is encapsulated either after or during the formation of vesicles, and administered subsequently. The drug can be soluble in water or in a non-polar solvent. These vehicle/drug systems are stable for at least 2 hours. The permeability of vesicles derived from mixed fluorocarbon/hydrocarbon amphiphiles to a drug such as adriamycin is lesser than that observed with vesicles formed with the related hydrocarbon/hydrocarbon amphiphile. However, both can be used to achieve controlled release of the drug.

The procedures used to prepare these lipidic membranes are well known to professionals and comprise techniques using solvents, injection, ultrasound or mechanical high-pressure homogenizers such as a Gaulin homogenizer or a microfluidizer.

In these preparations, the compound of the invention acts as a surfactant or co-surfactant, or dispersing agent, or as a vehicle to solubilize or disperse the drug in the preparation.

These compounds can thus be used in the pharmaceutical field to prepare drug compositions, using them as solubilizing, dispersing or emulsifying agents, in solutions or emulsions administrable, for example, orally, locally, parenterally, intraperitoneally, intravenously, intramuscularly or by injection.

The invention thus has also as its object emulsions comprising an oily phase, an aqueous phase and a surfactant constituted by a derivative of the invention.

In an emulsion of this type, other surfactants such as lecithins and copolymers of alkylenic oxide, for example of polyoxyethylene and polyoxypropylene, trishydroxymethyl aminomethane telomers and fluorinated surfactants, can be present. In these emulsions, the oily phase can be a hydrocarbon, a hydrofluorocarbon or a fluorocarbon or highly fluorinated compounds. In these emulsions, the oily phase, constituted for example by a fluorocarbon, can represent from 10% to 125% in w/v of the emulsion.

In these emulsions, the compounds of the invention used as surfactants are preferably compounds in which at least one of the $R^2$ and $R^3$ is a radical derived from a fluorocarbon.

Generally, the content in compound of the invention of these preparations is from 0.01 to 30% in weight/volume.

The aqueous phase may contain other additives such as antioxidants and agents to adjust the pH and the oncotic and osmotic pressures, in order to obtain injectable isotonic compositions.

The preparations can also be administered orally, locally, parenterally, intraperitoneally, intravenously, intramuscularly, sub-cutaneously or by inhalation.

In the case where, in the compounds used, $R^2$ and $R^3$ are both hydrocarbon radicals, or $R^2$ and $R^3$ are respectively a hydrocarbon radical and a fluorocarbon radical, the formation of liposomes has been demonstrated by electronic microscopy of their dispersions and by electronic microscopy after freeze-fracture.

Some of the vesicles formed with the compounds of the invention are stable over time and after sterilization at 121° C. for 15 min.

The preparations of the invention can also be used to modify the intravascular persistence, the biodistribution and/or the recognition of particles forming the dispersed system and for specific targeting of cells by these particles.

Other characteristics and advantages of the invention will be more clearly seen on reading the following examples, which are of course given as illustrations, and are not limitative, and on referring to the annexed schemes I and II.

EXAMPLES

Synthesis

See scheme 1, infra, for examples 1–11.

Example 1: Synthesis of Nα-[1-lactobionocarbonyl]-N-11[trieicos-1-en-yl] glycinamide, 6a A. Synthesis of the alcohol 1-trieicosen-11-ol, 1a $CH_2=CH-(CH_2)_8-CH[(CH_2)_{11}CH_3]OH$ A 1M commercial solution (45 ml) of dodecylmagnesium bromide in ether (4 $10^{-2}$ moles) was introduced into a tubular balloon flask fitted with a bromine ampulla and a refrigerant and swept by a current of dry nitrogen. 10-undecen-1-al (7.57 g; 0.045 moles) in 50 ml of anhydrous ether was added dropwise to the above solution. The reaction mixture was then maintained at boiling point for 1.5 h. The solution was cooled, and a saturated solution of ammonium chloride (100 ml) was added. The organic phases were washed with water, dried over sodium sulfate, then concentrated. The crude compound obtained was chromatographed over a short silica column (eluent hexane/ether 1/1). The pure product (14 g) was isolated in the form of a white powder. Yield 96%. m.p.: 63.8°–64.5° C. The $^1H$ and $^{13}C$ NMR spectra were in conformity with the expected structure. $^1H$ NMR ($CDCl_3$) 5.8 (1H, m, CH=); 4.9 (2H, m, $CH_2$=); 3.6 (1H, m, >CH): 2 (2H, td, =CH—$CH_2$); 1.3 (34H, m, $(CH_3)_{17}$); 0.9 (3H, t; $CH_3$).

B. Synthesis of 11-azido-1-trieicosen, 2a $CH_2=CH-(CH_2)_8-CH[(CH_2)_{11}CH_3]N_3$ 191 mg (1.1 mmol) of diethyl azodicarboxylate, 358 mg of alcohol 1a (1 mmol) and 288 mg (1.1 mmol) of triphenylphosphine in solution in anhydrous tetrahydrofurane (THF) were stirred for several minutes at room temperature. Diphenylphosphorylazide (302.5 mg; 1.1 mmol) was then added. This solution was treated with ultrasound for 15 minutes. After total disappearance of the alcohol, the THF was evaporated. The residue thus obtained was chromatographed over a silica column (eluent hexane). 350 mg of azide in an oil form were obtained. Yield=92%.

$^1H$ NMR ($CDCl_3$) 5.8 (1H, m, CH=); 4.9 (2H, m, $CH_2$=); 3.2 (1H, m, >$CHN_3$): 2 (2H, td, =CH—$CH_2$); 1.4 (36H, m, $(CH_2)_{18}$); 0.9 (3H, t; $CH_3$).

C. Synthesis of 11-amino-1-trieicosen, 3a $CH_2=CH(CH_2)_8-CH[(CH_2)_{11}CH_3]NH_2$ Azide (3 g; $8.28.10^{-3}$ moles) was dissolved in 150 ml of anhydrous ethylic ether. To the cooled solution, a solution of 1M of aluminum lithium hydride ($LiAlH_4$) (10 ml; 10 moles) in ether was slowly added at 0° C. After 15 minutes, the reduction of the azide was complete. Excess $LiAlH_4$ was removed by adding a few millilitres of water. After filtration, the ether phases were dried over sodium sulfate and concentrated. The amine (2.8 g oil, 98%) was isolated in the form of a yellow oil.

$^1H$ NMR ($CDCl_3$) 5.8 (1H, m, CH=); 4.9 (2H, m, $CH_2$=); 2.7 (1H, m, >$CHNH_2$): 2 (2H, td, =CH—$CH_2$); 1.3 (34, m, $(CH_2)_{17}$); 0.9 (3H, t; $CH_3$).

D. Synthesis of N-α-[tertiobutyloxycarbonyl]N-11[trieicos-1-en-yl] glycinamide, 4a $(CH_3)_3COC(O)NHCH_2C(O)NHCH[(CH_2)_{11}CH_3][(CH_2)_8CH=CH_2]$ The amine 3a (0.919 g; $2.72.10^{-3}$ moles), dicyclohexyl carbodiimide (DCC) (0.675 g; 3.27 $10^{-3}$ moles), N-tertiobutyl-oxycarbonyl glycine (BocglyOH) (0.573 g; 3.27 $10^{-3}$ moles) and hydroxybenzotriazole (HOBT) (100 mg) were added to 20 ml of anhydrous methylene chloride. After stirring for 15 minutes at room temperature, the reaction was complete. The dicyclohexylurea (DCU) formed was filtered, the solvent was evaporated, and the residue was chromatographed over silica (eluent hexane/ether 5/5). 1.350 g (97%, wax) of product 4a were obtained.

$^1H$ NMR ($CDCl_3$) 6.14 (1H, d, NH); 5.8 (1H, m, CH=); 5.43 (1H, t, NH); 4.9 (2H, t, CH2=); 3.9 (1H, m, >CH); 3.7 (1H, d; $CH_2C$); 2 (2H, td, >CH—$CH_2$); 1.5 (9H, m, $(CH_3)_3$); 1.3 (34H, m; $(CH_2)_{17}$); 0.9 (3H, t; $CH_3$).

E. Synthesis of N-α-1-lactobionocarbonyl-N-11-[trieicos-1-en-yl ]glycinamide, 6a.

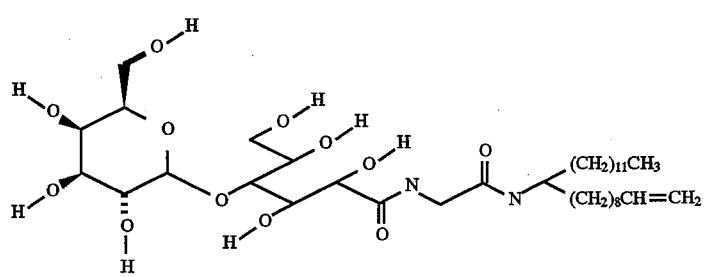

E.1 Synthesis of 1,5-lactobiono lactone (5a)

Lactobionic acid (0.947 g; $2.64.10^{-3}$ moles) methoxyethanol (30 ml), toluene (30 ml) and trifluoroacetic acid (TFA) (1 drop) were stirred and concentrated in a rotavapor. This operation was repeated 3 times, but without adding the trifluoroacetic acid. 1,5lactobiono lactone (0.902 g) was obtained.

E.2 Deprotection of the amine of 4a

A solution of 1.350 g (2.65.10$^{-3}$ moles) of 4a in $CH_2Cl_2$ to which trifluoroacetic acid (4.5 ml) has been added was stirred for 1 h at room temperature under nitrogen. The solvents and reactants were then evaporated. The salt was recovered.

E.3 Synthesis of 6a

Condensation between the amine and the 1,5-lactobiono lactone was realized at pH=8 in boiling methanol. When the reaction was complete, product 6a was chromatographed over a silica column (eluent AcOEt/methanol/water 80/18/2). 970 mg of the product (1.29.10$^{-3}$ moles) were isolated. Yield 63.5%. m.p.=188° C. (decomposition). (αD)$^{20}$ :+19 (C1, CHCl$_3$); (αD)$^{20}$:+15.4 (C, 1, MeOH).

$^1$H NMR (DMSO): 7.9 (1H, t, NH); 7.3 (1H, d, NH); 5.8 (1H, m, CH=); 5 (2H, t, CH$_2$=); 2 (2H, td, CH$_2$CH=)0.9 (3H, t, CH3).

Example 2: A. Synthesis of N-α-[1-lactobionocarbonyl]-N-3-[1-(perfluorooctyl)tridec-12-enyl] glycinamide, 6b

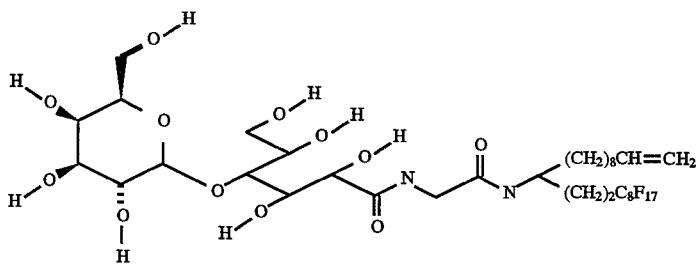

The procedure is identical to that followed for Example 1. Starting from the 1H, 1H, 2H, 2H-perfluorodecyl iodide and 10-undecen-1-ol. Compound 6b was obtained with an overall yield of 30%. The product was in the form of a white powder. m.p.=175° C. (decomposition). (αD)$^{20}$=+13° (C, 1, DMSO).

$^1$H NMR (DMSO): 7.98 (1H, d, NH); 7.5 (1H, t, NH); 5.8 (1H, m, CH=); 2.15 (2H, m, CH$_2$CF$_2$); 2 (2H, td, =CH—CH$_2$); 1.66–1.53 (2H, m, CH$_2$-CH$_2$CF$_2$);1.34 (14H, m (CH$_2$)$_{17}$);.

Example 3: A. Synthesis of N-α-1-[lactobionocarbonyl]-N-3-[1-(perfluohexyl)tridec-12-enyl] glycinamide, 6c

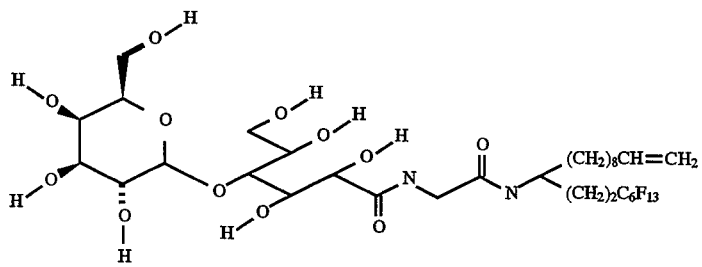

The procedure is identical to that followed for Example 1. Starting from the 1H, 1H, 2H, 2H-perfluorooctyl iodide and 10-undecen-1-ol, compound 6c (white powder) was obtained with an overall yield of 35%. m.p.=179° C. (αD)$^{20}$=+15.4 (C, 1, DMSO). $^1$H NMR (DMSO): 8 (1H, d, NH); 7.5 (1H, t, NH); 5.8 (1H, m; CH=); 4.9 (2H, m, CH$_2$=); 2.3–2.15 (2H, m, CH$_2$—CF$_2$); 2 (2H, td, CH$_2$—CH=); 1.68–1.4 (2H, m, CH$_2$—CH$_2$CF$_2$); 1.3 (14H, m (CH$_2$)$_7$).

Example 4: Synthesis of N-α-1-[lactobionocarbonyl]-N-12-[tetraeicosyl] glycinamide, 6d The procedure is identical to that followed for Example 1. The overall yield was 43%. m.p.=154° C. (αD)$^{22,4}$=+13.2 (C, 1, DMSO). $^1$H NMR (DMSO): 7.9 (1H, t, NH); 7.35 (1H, d, NH); 1.23 (42H, m, (CH$_2$)$_{21}$; 0.87 (6H, t, (CH$_3$)$_2$).

Example 5: Synthesis of N-α-1-[lactobionocarbonyl]-N-3-[1-(perfluorohexyl) dodecyl] glycinamide, 6e The procedure is identical to that followed for Example 1. Overall yield of 20%. m.p.=200° C. (αD)$^{22,24}$=+13.3 (C, 1, DMSO). $^1$H NMR (DMSO): 8 (1H, d, NH); 7.4 (1H, t, NH); 2.2 (2H, m, CH$_2$—CF$_2$); 1.8–1.6 (2H, m, CH$_2$—CH$_2$CF$_2$); 1.3 (16H, m (CH$_2$)$_8$); 0.9 (3H, t, CH$_3$).

Example 6: Synthesis of N-α-1-[lactobionocarbonyl]-N-3-[1-(perfluorooctyl) dodecyl]glycinamide, 6f The procedure is identical to that followed for Example 1. Overall yield of 13%. m.p.=163° C. (αD)$^{22,4}$=+12.9 (C, 1, DMSO). $^1$H NMR (DMSO): 8 (1H, d, NH); 7.45 (1H, t, NH); 2.16 (2H, m, CH$_2$—CF$_2$); 1.68 (2H, m, CH$_2$—CH$_2$CF$_2$); 1.36–1.32 (16H, m (CH$_2$)$_8$); 0.85 (3H, t, CH$_3$).

Example 7: Synthesis of 6-(perfluorohexyl)-4-thiahexanal $C_6F_{13}CH_2CH_2SCH_2CH_2CHO$ To 2.5 ml of acrolein (3.64 10$^{-2}$ mole), 13.8 g of $C_6F_{13}CH_2CH_2SH$ (3.64.10$^{-2}$ mole) and 30 ml of acetonitrile, 100 mg of AIBN were added. The mixture was brought to boiling point for 2 days under nitrogen. After evaporation of the solvent, chromatography on silica gel (eluent hexane/ethyl acetate 8/2). 10.3 g of aldehyde were obtained (yellow liquid, 65%).

$^1$H NMR (CDCl$_3$): 9.79 (1H, s, C$\underline{H}$O); 2.83 (6H, m, 3CH$_2$); 2.43 (2H, m, C$\underline{H}_2$CF$_2$). IR(CCl$_4$); C=O 1728 cm$^{-1}$ Synthesis of 1,8-di-(perfluorohexyl)-6-thia-3-octanol C$_6$F$_{13}$(CH$_2$)$_2$(CH$_2$)2CH [(CH$_2$)$_2$C$_6$F$_{13}$]OH, 1g Process identical to 1b. From 15.2 g (3.2.10$^{-2}$ mole) of C$_6$F$_{13}$CH$_2$CH$_2$I and 17 g of C$_6$F$_{13}$CH$_2$CH$_2$SCH$_2$CH$_2$CHO (3.89.10$^{-2}$ mole), 16 g of alcohol 1g were obtained. Yield 58%. m.p.=50.8° C.

$^1$H NMR (CDCl$_3$): 3.9 (1H, m, CH); 2.8 (4H, m, 2(C$\underline{H}_2$)S); 2.38 (4H, m, 2C$\underline{H}_2$CF$_2$); 1.77 (4H, m, C$\underline{H}_2$CH)

Synthesis of 3-azido-1,8-di-(perfluorohexyl)-6-thiaoctane C$_6$F$_{13}$(CH$_2$)$_2$S(CH$_2$)$_2$CH[(CH$_2$)$_2$C$_6$F$_{13}$]N$_3$, 2g Process identical to 2a. From 9 g of alcohol 3.6 g of azide 2g (oil, yield 39%) were isolated $^1$H NMR (CDCl$_3$): 3.6 (1H, m, CH); 2.8 (4H, m, 2C$\underline{H}_2$S); 2.36 (4H, m, 2C$\underline{H}_2$CF$_2$); 1.83 (4H, m, 2C$\underline{H}_2$CH).

Synthesis of N-[tertiobutyloxycarbonyl]-N-3-[1,8-di(perfluorohexyl)-6-thia-octyl] glycinamide (CH$_3$)$_3$COC(O)NHCH$_2$C(O)NHCH[(CH$_2$)$_2$S (CH$_2$)$_2$C$_6$F$_{13}$][(CH$_2$)$_2$C$_6$F$_{13}$], 4g Process identical to 4a. From 3.6 g of azide 2g 2.29 g of 4g (wax, 55%) were isolated.

$^1$H NMR (CDCl$_3$): 7 (1H, m, NH); 5.87 (1H, m, NH); 4.13 (1H, m, CH); 3.79 (2H, m, NCH$_2$C(O)); 2.74 (2H, m, C$\underline{H}_2$S); 2.65 (2H, m, C$\underline{H}_2$S); 2.5-2 (4H, m, 2C$\underline{H}_2$CF$_2$); 2-1.69 (4H, m, 2C$\underline{H}_2$CH); 1.44 (9H, m, (CH$_3$)$_3$).

Synthesis of Nα-1-[lactobionocarbonyl]-N-3-[1,8-di(perfluorohexyl)-6-thia-octyl] glycinamide, 6g Process identical to 6a. from 1.5 g of 4g, 1.3 g of product 6g (68%) were obtained. Decomposition at 181.9° C.

$^1$H NMR (DMSO): 7.99 (1H, m, NH); 7.54 (1H, m, NH); 2.72 (2H, m, CH$_2$S); 2.50 (6H, m, C$\underline{H}_2$S+2C$\underline{H}_2$CF$_2$); 2.17 (2H, m, CH$_2$CH); 1.67 (2H, m, C$\underline{H}_2$CH).

Example 8 : Synthesis of 1-azido-1H, 1H, 2H, 2H-perfluorooctane C$_8$F$_{17}$CH$_2$CH$_2$N$_3$, 2h 15 g (3.16.10$^{-2}$ mole) of C$_6$F$_{13}$CH$_2$CH$_2$I were dissolved in 25 ml of dimethylformamide (DMF); 1 g of NaN$_3$ were added. The mixture was shaken during 16 h at room temperature, than added to 300 ml of cold water. The solution was extracted with ether. After drying and concentration, an oil was recovered which was distilled under reduced pressure leading to 7.5 g of azide (Eb=30° C., P=0.5 mbar). yield 61%

$^1$H NMR (CDCl$_3$): 3.60 (2H, m, C$\underline{H}_2$CH$_2$CF$_2$); 2.38 (2H, m, C$\underline{H}_2$CF$_2$).

Synthesis of Nα-[tertiobutyloxycarbonyl]-N-1-[2-(perfluorohexyl)-ethyl] glycinamide (CH$_3$)$_3$COC(O)NHCH$_2$C(O)NH(CH$_2$)$_2$C$_6$F$_{13}$, 4h To 3.5 g of C$_6$F$_{13}$CH$_2$CH$_2$N$_3$ in 50 ml of anhydrous ether 10 ml of a solution of LiAlH$_4$ (1M in ether) were added. The reduction of the azide was complete in 15 min. After destruction of the excess of LiAlH$_4$, filtration of the aluminium hydroxyde formed, the ether phase was dried and concentrated. 3.2 g of amine (98%) were isolated.

The amine obtained was allowed to react in dichloromethane in the presence of 1.8 g (8.8 mmole) of dicyclohexylcarbodiimide, 1.53 g (8.8 mmole) of N-tertiobutyloxycarbonylglycine and 100 mg of hydroxybenzotriazole (HOBT). After stirring for 15 min at room temperature, the dicyclohexylurea (DCU) formed was filtered, the solvent evaporated and the residue was chromatographed on a silica gel column (eluent hexane/ether 5/5). 4.4 g of compound 4h were obtained (96%). m.p.=78° C.

Synthesis of Nα-1-[lactobionocarbonyl] N-1-[2-(perfluorohexyl)ethyl]glycinamide, 6h Process identical to 6a. from 2 g of 4h; 2.4 g of 6h (80%) were obtained.

m.p. : 145° C. (decomposition).

$^1$H NMR (DMSO): 7.97 (1H, m, NH); 7.45 (1H, m, NH); 2.38 (2H, m, C$\underline{H}_2$CF$_2$); 1.67–1.36 (2H, m, C$\underline{H}_2$CH$_2$CF$_2$).

Example 9: Synthesis of 1-azido-1H,1H,2H,2H-perfluorodecane C$_8$F$_{17}$CH$_2$CH$_2$N$_3$, 2i Process identical to 2h. From 9 g of C$_8$F$_{17}$CH$_2$CH$_2$I, 4.6 g of 2h (oil, 60%) were obtained.

$^1$H NMR (CDCl$_3$): 3.60 (2H, m, C$\underline{H}_2$CH$_2$CF$_2$); 2.37 (2H, m, C$\underline{H}_2$CF$_2$).

Synthesis of Nα-[tertiobutyloxycarbonyl]-N-1-[2-(perfluorooctyl)ethyl] glycinamide, 4i Process identical to 4h. From 3 g of C$_8$F$_{17}$CH$_2$CH$_2$N$_3$, 3.3 g of 4i (wax, 96%) were isolated.

$^1$H NMR (CDCl$_3$): 6.5 (1H, m, NH); 5.0 (1H, m, NH); 3.77 (2H, d, CH$_2$C(O)); 3.61 (2H, m, C$\underline{H}_2$CH$_2$CF$_2$); 2.32 (2H, C$\underline{H}_2$CF$_2$).

Synthesis of Nα-1-[lactobionocarbonyl]-N-1-[2-(perfluorohexyl)ethyl] glycinamide, 6i Process identical to 6h. From 3.3 g of 4i, 3.6 g of 6i (80%) were obtained. m.p.=148° C. (decomposition)

$^1$H NMR (CDCl$_3$): 8.6 (1H, m, NH); 7.98 (1H, m, NH); 5.2–3 (23H); 2.4 (2H, m, C$\underline{H}_2$CF$_2$).

Example 10 Nα-(Nα-1-lactobionocarbonyl)-glycyl) N-3-[1-(perfluorohexyl)dodecyl] glycinamide, 7a Synthetic procedure identical to 6e. 7a was isolated in 64% yield.

F=181° C. (decomposition)·[α]D=+15.2 (C, 1, DMSO). $^1$H NMR (DMSO d$_6$): 8.05 (2H, m, NH); 7.55 (1H, d, d, NH); 2.2 (2H, m, C$\underline{H}_2$CF$_2$); 1.58 (2H, m, C$\underline{H}_2$CH$_2$CF$_2$); 1.44 (2H, m) ; 0.86 (3H, t, CH$_3$).

19F NMR (DMSO d$_6$) : −79.81; −112.79; −121.31; −122.38 (4F); −125.34.

Example 11 N-α-(N-α-1-lactobionocarbonyl)-glycyl-N-11-(trieicos-1-enyl) glycinamide, 7b Synthetic procedure identical to 6a. 6b was isolated in 80% yield. F=175–182° C. (decomposition). [α]D=+19.2 (C, 1, DMSO). $^1$H NMR (DMSO d$_6$): 8 (2H, m, NH); 7.4 (1H, d, NH); 5.78 (1H, m, CH=); 5.44 (1H, d, OH); 5.2 (1H, d, OH); 5.0 (2H, m, CH2=); ; 2 (2H, td, CH$_2$CH=); 1.25 (36H, m, (CH$_2$)18); 0.8 +(3H, t, CH$_3$).

Scheme I

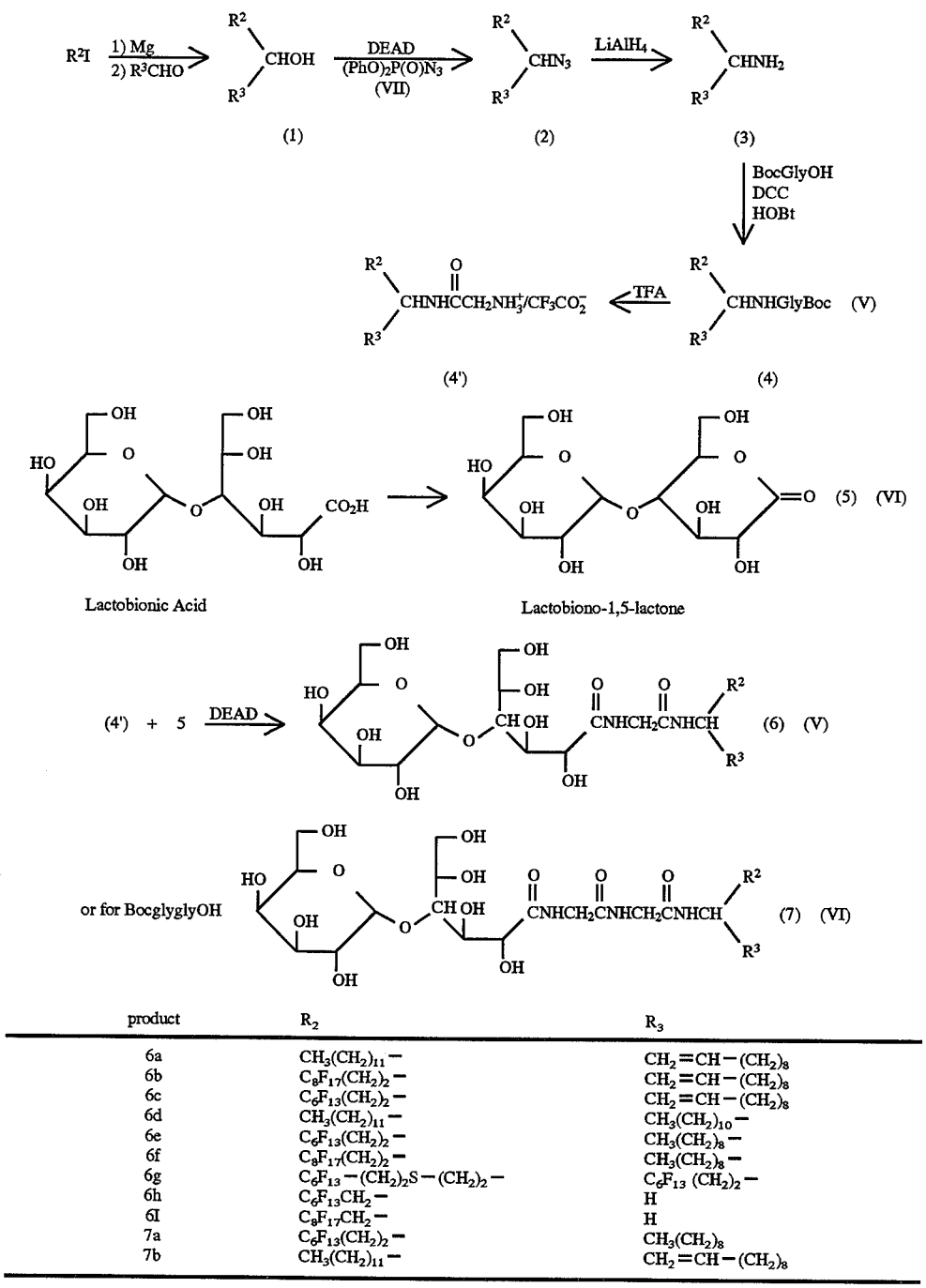

Lactobionic Acid → Lactobiono-1,5-lactone

| product | R₂ | R₃ |
|---|---|---|
| 6a | $CH_3(CH_2)_{11}-$ | $CH_2=CH-(CH_2)_8$ |
| 6b | $C_8F_{17}(CH_2)_2-$ | $CH_2=CH-(CH_2)_8$ |
| 6c | $C_6F_{13}(CH_2)_2-$ | $CH_2=CH-(CH_2)_8$ |
| 6d | $CH_3(CH_2)_{11}-$ | $CH_3(CH_2)_{10}-$ |
| 6e | $C_6F_{13}(CH_2)_2-$ | $CH_3(CH_2)_8-$ |
| 6f | $C_8F_{17}(CH_2)_2-$ | $CH_3(CH_2)_8-$ |
| 6g | $C_6F_{13}-(CH_2)_2S-(CH_2)_2-$ | $C_6F_{13}(CH_2)_2-$ |
| 6h | $C_6F_{13}CH_2-$ | H |
| 6I | $C_8F_{17}CH_2-$ | H |
| 7a | $C_6F_{13}(CH_2)_2-$ | $CH_3(CH_2)_8$ |
| 7b | $CH_3(CH_2)_{11}-$ | $CH_2=CH-(CH_2)_8$ |

Example 12 : (Scheme II) Synthesis of Nα-1-(3-perfluoroctyl)propionocarbonyl(εN-1-lactobionocarbonyl)-N-[1-undecyl] lysinamide, 6j A. Synthesis of BocLys(Z)C(O)NH(CH₂)₁₀CH₃, 1j To a dichloromethane solution of 2.29 g (1.34.10⁻² mole) of undecanamine (CH₃(CH₂)₁₀NH₂), 5 g (1.34.10⁻² mole) of BocLys(Z)OH, 2.75 g of DCC and 200 mg of HOBT were added. The mixture was allowed to react for 24 h. The DCU was filtered, and the solution was concentrated yielding 7.2 g of crude product which is used as such in the following step.

B. Synthesis of Lys(Z) [C(O)NH(CH₂)₁₀CH₃] [NHC(O)(CH₂)₂C₈F₁₇], 2j

The 7,2 g of 1j were dissolved in 30 ml of dichloromethane and 15 ml of trifluoroacetic acid were added. The Boc group was immediately removed. After concentration, adding of ether and washing with NaHCO₃, the organic phase was dried and concentrated. The Lys(Z)[C(O)NH(CH₂)₁₀CH₃][NH₂] formed was allowed to react with C₈F₁₇CH₂CH₂CO₂H (7,6 g, 1,34.10⁻² mole); 2.7 g of DCC (1.34.10⁻² mole) and 100 mg of HOBT. The peptidic coupling was carried out in dimethylformamide (DMF). After 24 h the DCU was filtered and the product was crystallized.

C. Synthesis of N-1-[3-(perfluorooctyl)propionocarbonyl (ε-N-1-lactobionocarbonyl) 1-undecane] lysinamide, 3j 1 g of 2j was dissolved in methanol, Z was deprotected by hydrogenation yielding 0.82 g (96%) of deprotected product. 0.622 g ($8.10^{-4}$ mole) of the amine were allowed to react with 0.27 g ($7.9.10^{-4}$ mole) of lactobiono-1,5 lactone in boiling methanol. After 24 h, the product was purified by chromatography on silica gel (eluent AcOEt/MeOH/H$_2$O 80/18/2) yielding 62 mg of 3j.(72%). m.p.=171° C. (decomposition) $(\alpha D)^{20}$=+13 (C, 1, DMSO) $^1$H NMR (DMSO): 8.165 (1H, d, NHC(O)); 7.83 (1H, m, C(O)NH); 7.59 (1H, m, C(O)NH).

mole.dm$^{-3}$ by 100 KGy γ radiation, in a source of γ rays of $^{60}$Co of 1.5 KGyh-1 (Larabee L. E. et al, J. Polym. Sci. Polym. Lett. Ed. 1979, 17, 749).

The formation of the polymer is supported by proton NMR (disappearance of the vinylic proton signals and enlargement of the other signals).

Example 14: Preparation of vesicles from product 6a

Product 6a (30 mg) was dissolved in a mixture of chloroform/methanol (1/1 v/v) in a round 4 mL tube. The solvent was evaporated in a rotavapor until a uniform film was obtained. The remaining traces of solvent were eliminated under vacuum. Water for injectable preparations (3.97

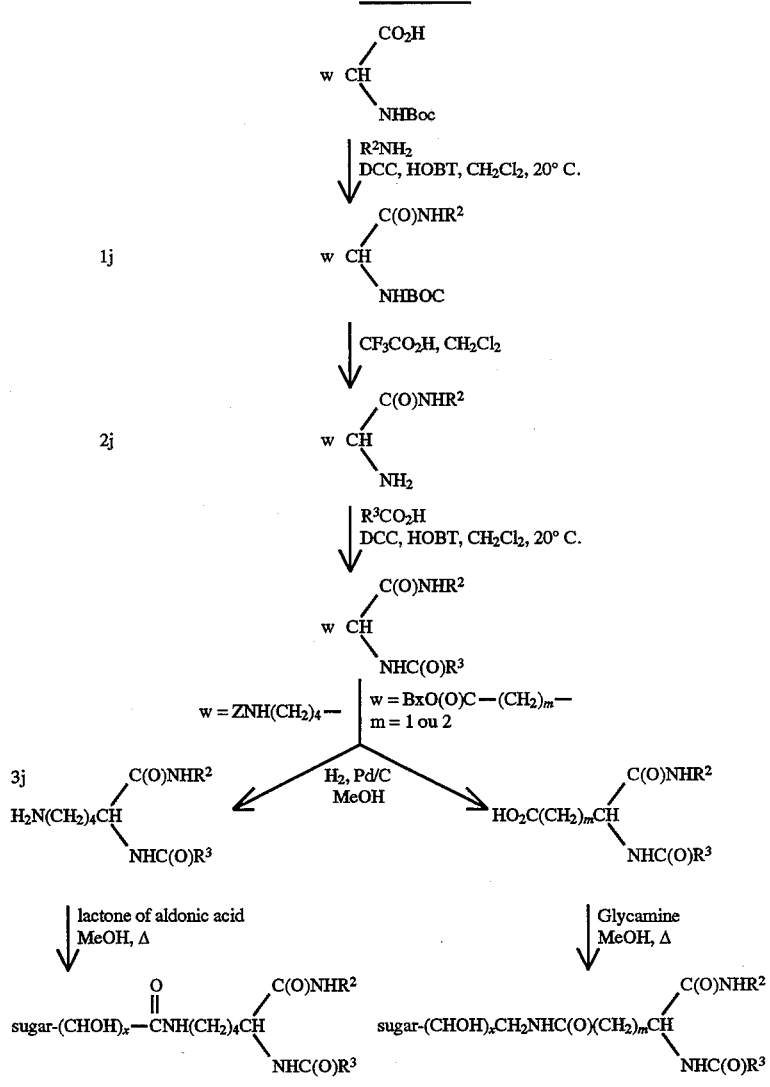

Example 13: Polymerization of products 6a and 6b

The polymerization was effected by irradiation of the aqueous dispersion of the products at a concentration of 0.1 mL) was added to the dried product. After stirring with a Vortex for 3 minutes, sonication (BRANSON B30, 7 mm probe, Power 5, pulsed mode 50, 15 minutes) at 20° C.

above the phase-transition temperature gave a bluish dispersion. Measurement of particle sizes, (Coulter model N4MD SUB-MICRON particle analyzer) indicated that the dispersion remained stable for at least 1 month, average Φ=49 nm. Sterilization of such a dispersion at 121° C. for 15 minutes did not significantly modify these vesicles (Φ before and after sterilization=58 and 61 nm, respectively).

Example 15: Preparation of vesicles from product 6d.

The procedure of example 14 when applied to product 6d ($10^{-2}$M) led to the formation of vesicles as shown by electronic microscopy.

Example 16: Preparation of vesicles from product 6e

The procedure described in example 14 when applied to product 6e ($10$M$^{-2}$, sonication 20 minutes) led to the formation of vesicles which after sterilization had an average diameter of 318 nm.

Example 17: Preparation of vesicles from product 6b

The procedure described in example 14 when applied to product 6b ($10^{-2}$M) led to the formation of vesicles observed by electronic microscopy.

Example 18: Preparation of vesicles from product 7a

Product 7a ($10^{-2}$M) forms monolayered vesicles almost instantaneously upon dispersion with water as observed by electronic microscopy.

Example 19: Preparation of vesicles from product 7b

Product 7b ($10^{-2}$M) forms monolayered vesicles almost instantaneously upon dispersion with water as observed by electronic microscopy.

Structural Study

Example 20: Identification of the vesicles by transmission electronic microscopy:

The formation of vesicles was observed by transmission electronic microscopy by the negative staining method. The lipidic dispersion was applied on a grid covered with FORMVAR membrane. The sample was colored by depositing of a drop of phosphotungstic acid (2%, pH adjusted to 7) for 1 min; The excess acid was removed using a filter paper. The grid was then dried and the sample was examined using a PHILIPS microscope (CM2 Model) at 80 Kv.

The formation of vesicles was also observed after dispersion of the product 6a, 7a, 7b. FIG. 1 is a micrography obtained in these conditions on a $10^{-2}$M dispersion of product 6a.

Example 21

Observation of the vesicles by electronic microscopy after freeze-fracture.

One drop of lipidic dispersion (about 0.5 mL) was placed on a copper support. Freezing was realized by rapid immersion in liquid propane (−196° C.). The fractures were realized using a Balzers BAF 300 at −120° C. under $10^{-6}$ mmHg with a knife cooled to −150° C. The replicas were obtained by depositing a platinum layer (10–20 A) under an angle of 35° then carbon (110–120 A) with an angle of 90°. The replicas were then immersed in water, washed, placed on a copper grid (3 mm, 300 mesh) and examined with a HITACHI 600 electronic microscope (H600) at 75 KV. The formation of vesicles was established by this method for products 6b, 7a, 7b. FIG. 2 represents the photomicrographs obtained on $10^{-2}$M dispersions of products 6b, 7a, 7b.

Differential scanning calorimetry

The phase transition temperatures and the transition enthalpies were determined after hydration by a known quantity of water using a SETARAM DSC-92 apparatus.

Example 22

Product 6d (16 mg) was hydrated with 10.2 mL of a mixture of water/ethylene glycol 60/40 (hydratation percentage 28%). Heating and cooling between −10° C. and 45° C. at a speed of 2° C./min showed that the Tc was found to be at 14° C. and that the transition enthalpy was −10.29 mcal/mg.

Example 23

Product 6a (10.8 mg) was hydrated with a mixture of water/ethylene glycol 60/40 (hydration percentage 37%). The Tc was found to be 22° C. and that the transition enthalpy was −11.6 mcal/mg.

Biocompatibility

Example 24

In vivo toxicity of product 6i in mice. A rapid intravenous injection into the caudal vein, of 0.5 mL (25 mL/kg animal body weight) of a solution of 6i in physiological water, to which Pluronic F-68 was added as dispersant (25/10 g/L, 6i/Pluronic F-68) was made. This product was tolerated at a dose of 625 mg/kg in weight; no deaths occurred after 1 month of observation, among the 10 animals treated.

In vivo toxicity of products 6a, 6b, 6c in mice. A rapid intraperitoneal injection was made, of 0.5 mL (25 mL/kg animal body weight, n=10) of a dispersion of these products in physiological water. The products were tolerated at a dose of 500 mg/kg body weight; no deaths occurred after 1 month of observation of the 10 animals treated.

Example 25

The hemolytic activity of products 6h, 6i was determined by adding 2 mL of a solution of these products in physiological water to an equal volume of a 1% suspension of human erythrocytes in an isotonic phosphate buffer. After an hour of incubation at 37° C. the solutions were centrifuged. The degree of hemolysis was determined spectrophotometrically (540 nm) by comparing the quantity of hemoglobin liberated in the supernatant. Compounds 6h, 6i were not hemolytic at a concentration of 50 g/l.

Example 26

The toxicity of products 6a and 6e was determined on lymphoblastoid cell cultures of the Namalva type in an RPMI medium containing 10% of foetal calf serum at 37° C. under 7% $CO_2$, according to the method described by M. Le Blanc et al in Pharm. Res. 195 (1988). Compounds 6a, 6e, 6h, 6i did not affect the growth and viability of the cells after 4 days at 37° C..

Encapsulation of Adriamycin in Liposomes Formed With Compounds of the Invention, and Stability of the Resulting Systems.

Example 27

An aqueous dispersion of compound 7b (141 g, 60 mM) in citric acid (2 ml, 1M pH=4) was prepared (sonication, probe 3 mm, power5, room temperature, 5 min, mean diameter=35 nm). The liposomal dispersion was then passed through a sephadex column and centrifugation was achieved at 2500 rpm during 4 minutes. Adriamycin (12 ml, 30 mM) was added to the liposomal dispersion. The amount of drug encapsulated, the stability of encapsulation over time and the release of adriamycin were measured.

The kinetics of release were determined at 37° C. At different times the release was stopped by adding 650 ml of sucrose buffer at 4° C. (0.3M, pH=7.5) to 150 ml of liposomal dispersion, then 21 ml of NaOH (1N). The $DO_i$ of the solution was measured, which correspond to the quantity of adriamycin outside the liposomes. After that, liposomes were lysed by the addition of 10ml of Triton (20% w/v). The final DO ($DO_f$) was measured which corresponds to the total quantity of adriamycin. ($DO_f-DO_i$)/$DO_f$ gives the quantity of adriamycin remaining inside the liposomes. This experience showed that the amount of encapsulated adriamycin was about 77% after 20 min and 59% after 120 min.

Example 28

The same experiment was done with compound 7a. 177 mg of 7a were added to 3 ml of citric acid (1M), agitated for a few seconds and sonication at room temperature. The pH gradient was established on a Sephadex column G50 with tris-HCl buffer. Measurement of the optical density showed that the amount of encapsulated adriamycin was 66% after 10 min and 60% after 120 min.

There will be various modifications, improvements, and applications of the disclosed invention that will be apparent to those skilled in the art, and the present application is intended to cover such embodiments. Although the present invention has been described in the context of certain preferred embodiments, it is intended that the full scope of the invention be measured by reference to the following claims.

What is claimed is:

1. A composition for biomedical use, comprising:

a biologically active compound; and an amphiphilic compound derived from an amino acid or peptide and having the formula $$X—R^1—AA—Y^1—\underset{R^3}{\overset{R^2}{\underset{|}{\overset{|}{CH}}}}; \quad (I)$$

or $$X—R^1—R^4—\underset{Y^3R^3}{\overset{ZY^2R^2}{\underset{|}{\overset{|}{CH}}}} \quad (II)$$

wherein (a) X is a polyhydroxylated hydrophilic moiety selected from the group consisting of sugars, polyols, aminopolyols and oligosaccharides;

(b) $R^1$ represents a bivalent radical derived from a monosaccharide in an open form and having the formula:

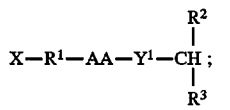
(III)

(IV)

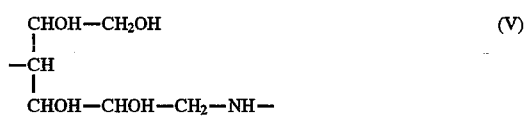
(V)

(c) AA is an amino acid or peptide moiety;

(d) $Y^1$ is —NH, —S—, —CO—, —O—, or —C(O)—$(CH_2)_L$—, wherein L is 1 or 2;

(e) $R^2$ and $R^3$, which can be identical or different, are H; a linear or branched, saturated or unsaturated $C_{5-20}$ hydrocarbon; or a linear or branched, saturated or unsaturated $C_{5-20}$ fluorinated hydrocarbon or fluorocarbon radical wherein 50 to 100% of the hydrogen atoms have been replaced by fluorine atoms, said hydrocarbon, fluorinated hydrocarbon or fluorocarbon radical optionally having one or more O and S atoms within the C chain, and optionally having the hydrogen atoms of said radical replaced by one or more chlorine or bromine atoms; and an unsaturated terminal group having the formula:
—O—CH=$CH_2$;
—OC(O)$CR_5$=$CH_2$;
—C(O)—$CR_5$=$CH_2$; or.
—NHC(O)$CR_5$=$CH_2$ in which $R^5$ is H or $CH_3$, provided that $R^2$ and $R^3$ do not both represent H;

(f) $R^4$ represents

—CO$(CH_2)_m$— with $0 \leq m \leq 2$;
—NH$(CH_2)_n$— with $0 \leq n \leq 4$;
—O—$CH_2$—;
—O—$\underset{CH_3}{\overset{|}{CH}}$—;

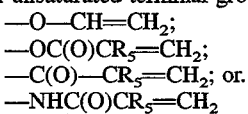

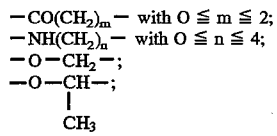

—NH—$CH_2$—CH(OH)—$(CH_2)_2$—;
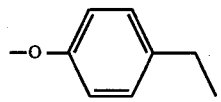

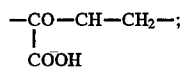

—AA—CO—$(CH_2)_m$ with $0 \leq m \leq 2$;
—AA—NH—$(CH_2)_n$ with $0 \leq n \leq 4$;
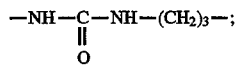

—AA—NH—$CH_2$—CH(OH)—$(CH_2)_2$—;
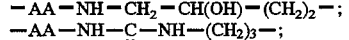

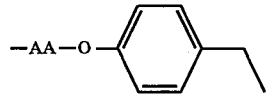

-continued

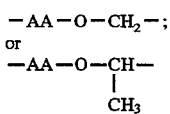

wherein AA is an amino acid or peptide;
(g) $Y^2$ and $Y^3$, which are different, are $-(CH_2)_mC(O)-NH-$ with $0 \leq m \leq 2$;
$-(CH_2)_mC(S)-NH-$ with $0 \leq m \leq 2$;
$-(CH_2)_pO-$ with $0 \leq p \leq 2$;
$-(CH_2)_pOC(O)-$ with $0 \leq p \leq 2$
$-(CH_2)_s-$;
$-C(O)O-$;
$-C(O)S-$;
$-(CH_2)_nNHC(O)-$ with $0 \leq n \leq 4$;
$-(CH_2)_2-CH(OH)-CH_2-NH-C(O)-$;
$-(CH_2)_3-NH-C-NH-C(O)-$;
                    $\|$
                    $NH$ $-(CH_2)_3-NH-C(O)-NH-C(O)-$;

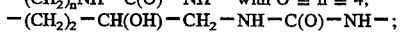

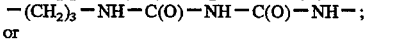

$-CH-O-$;
 $|$
 $CH_3$
$-CH-OC(O)-$;
 $|$
 $CH_3$
$-(CH_2)_nNH-C(O)-NH-$ with $0 \leq n \leq 4$;
$-(CH_2)_2-CH(OH)-CH_2-NH-C(O)-NH-$;
$-(CH_2)_3-NH-C(O)-NH-C(O)-NH-$;
or
$-(CH_2)_3-NH-C-NH-C(O)-NH-$
                $\|$
                $NH$ provided that at least one of the $Y^2$ and $Y^3$ represent —NH—C(O)— or —C(O)—NH—.

2. A composition according to claim 1, further comprising at least one additive chosen from among agents to control pH and antioxidants.

3. A composition according to claim 2 in combination with a natural or synthetic amphiphilic compound.

4. A composition according to claim 1, said composition comprising lipid vesicles in combination with said biologically active compound.

5. A composition according to claim 4, wherein said composition is stable after heat sterilization at temperatures of at least 121° C. for a period of 15 minutes at ambient pressures.

6. A composition according to claim 4 wherein said vesicles include an antitumor agent.

7. A composition according to claim 6, wherein the antitumor agent is selected from the group consisting of cis-platinum, 5-fluorouracil, adriamycine and combinations thereof.

8. A method for modifying natural or synthetic membranes, comprising the addition of an effective modifying concentration of a composition according to claim 1 to such membranes.

9. A composition according to claim 1 wherein each of R2 and R3 of said amphiphilic compound is independently selected from the group consisting of said hydrocarbon, said fluorinated hydrocarbon and said fluorocarbon radicals.

10. A composition according to claim 1 wherein each of R2 and R3 of said amphiphilic compound is a said fluorinated hydrocarbon or a said fluorocarbon radical.

11. A composition according to claim 1 wherein X of said amphiphilic compound is:

(h) a $C_1$ to $C_{24}$ saturated or unsaturated sugar, selected from the group consisting of tetroses, pentoses, hexoses, aminopentoses, aminohexoses, deoxypentoses, deoxyhexoses, disaccharides and oligosaccharides;

(i) a polyol which is (1) the hydrogenated form of a sugar derived from a member of the group consisting of tetroses, pentoses, hexoses, aminopentoses, aminohexoses, desoxypentoses, desoxyhexoses, disaccharides and oligosaccharides, (2) a cyclic hexitol, (3) a sugar or polyol as defined above in which one or several hydrogen atoms of the OH polyol or sugar groups have been replaced by an acetyl, benzyl, allyl, benzoyl, trityl, isopropylidene, benzylidene or cyclohexylidene group, by a group of formula $(CH_2CH_2O)_tR^6$), wherein t is an integer from 1 to 100 and $R^6$ is a hydrogen atom, or a linear or branched, saturated or unsaturated $C_1$ to $C_{24}$ hydrocarbon radical.

12. A composition according to claim 1 wherein said amphiphilic compound is of the formula:

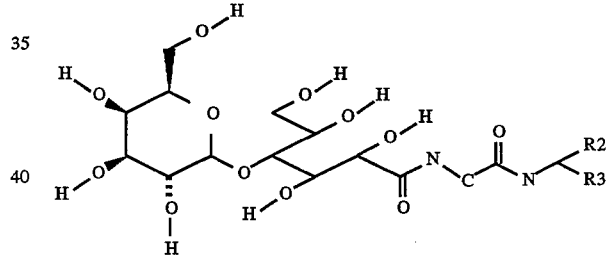

OR

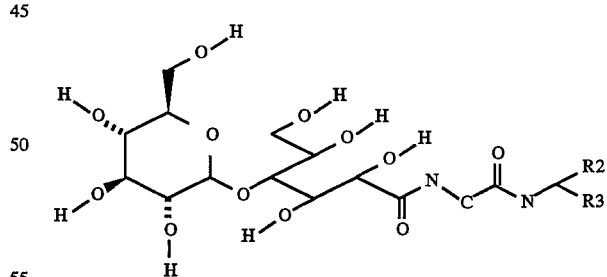

wherein $R^2$ represents $(CH_2)_{11}CH_3$;

$(CH_2)_2C_6F_{13}$; or $(CH_2)_2C_8F_{17}$ and $R^3$ represents $(CH_2)_8CH=CH_2$ or $(CH_2)_8CH_3$.

13. A composition according to claim 1 wherein said amphiphilic compound is of the formula:

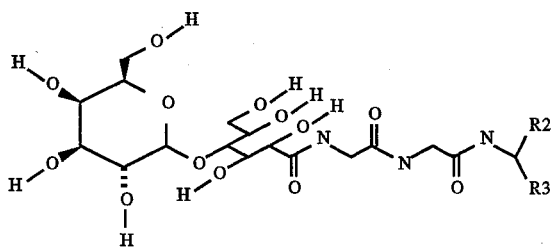

wherein R2 represents:

$(CH_2)_{11}CH_3$ or $(CH_2)_2C_6F_{13}$
and R3 represents
$(CH_2)_8CH=CH_2$ or $(CH_2)_8CH_3$.

14. A composition according to claim 1 wherein said amphiphilic compound is of the formula:

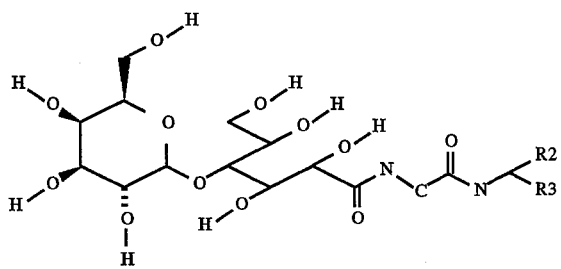

wherein $R^2$ represents
$(CH_2)_2C_6F_{13}$ or
$(CH_2)_2C_8F_{17}$
and $R^3$ represents a hydrogen atom.

15. A composition according to claim 1 wherein said amphiphilic compound is of the formula:

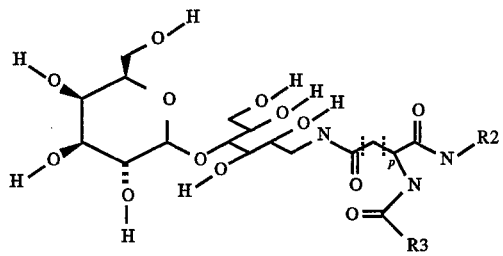

wherein p is equal to 1 or 2, $R^2$ represents $(CH_2)_2C_8F_{17}$, and $R_3$ represents $(CH_2)_2C_8F_{17}$;
$(CH_2)_{10}$—NH—C(O)—CH=CH_2;
$(CH_2)_{10}$—C(O)—CH=CH_2; or
$(CH_2)_9CH_3$.

16. A composition according to claim 1 wherein said amphiphilic compound is of the formula:

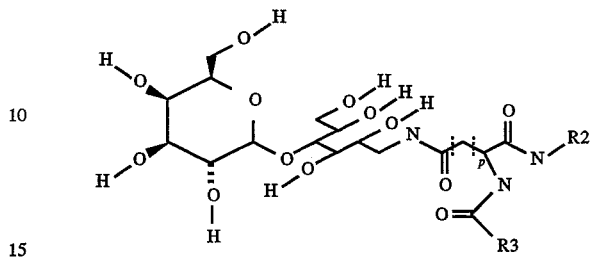

wherein p is equal to 1 or 2
$R^2$ represents $(CH_2)_{10}$—$CH_3$, and
$R^3$ represents $(CH_2)_9CH_3$ or $(CH_2)_8$—CH=CH_2.

17. A composition according to claim 1 wherein said amphiphilic compound is of the formula:

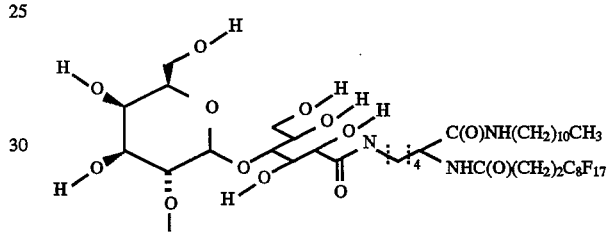

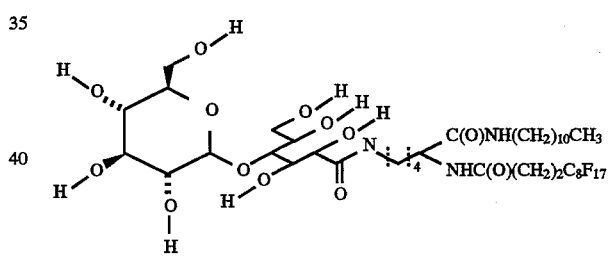

18. A composition according to claim 1 wherein said biologically active agent is a drug.

19. A composition according to claim 1 wherein said drug is selected from the group consisting of anti-inflammatory, analgesic, antitumoral, antibiotic and antiallergic agents.

* * * * *